United States Patent [19]

Mookherjee et al.

[11] Patent Number: 5,321,006
[45] Date of Patent: * Jun. 14, 1994

[54] FLAVOR AND FRAGRANCE COMPOSITIONS PRODUCED USING PROCESS FOR QUANTITATIVELY AND QUALITATIVELY SUBSTANTIALLY CONTINUOUSLY ANALYZING THE AROMA EMITTED FROM A LIVING FRUIT

[75] Inventors: Braja D. Mookherjee, Holmdel; Robert W. Trenkle, Brielle; Subha M. Patel, Bridgewater; Sharon M. Brown, Fair Haven, all of N.J.

[73] Assignee: International Flavors & Frgrances Inc., New York, N.Y.

[*] Notice: The portion of the term of this patent subsequent to Nov. 23, 2010 has been disclaimed.

[21] Appl. No.: 108,794

[22] Filed: Aug. 19, 1993

Related U.S. Application Data

[63] Continuation-in-part of Ser. No. 23,960, Feb. 26, 1993, Pat. No. 5,263,359, which is a continuation-in-part of Ser. No. 988,337, Dec. 9, 1992, Pat. No. 5,269,169.

[51] Int. Cl.$^5$ ............................................. A61K 7/46
[52] U.S. Cl. ........................................................ 512/5
[58] Field of Search ................................... 512/2, 5, 3

[56] References Cited

U.S. PATENT DOCUMENTS

| | | | |
|---|---|---|---|
| 409,859 | 8/1889 | Nellensteyn | 512/5 |
| 2,256,772 | 9/1941 | Freudenberg | 512/2 |
| 3,150,050 | 9/1964 | Safrin | 512/5 |
| 4,257,945 | 3/1981 | Martel | 512/5 |

OTHER PUBLICATIONS

Ciccioli, et al., Comm. Eur. Communities [Rep.] EUR 1984, EUR 9436, Phys.-Chem. Behav. Atmos. Pollut. 62-73 (abstracted at Chem. Abstracts vol. 102:208465n (1985).
Johansson, et al., J. Geophys. Res., [Atmos.], 1993, 98(D3), 5121-33 (abstracted at Chem. Abstracts vol. 119:164485p (Sep. 20, 1993)).
Adams, R. P., Mod. Methods Plant Anal. New Ser., 1991, 12 (Essent. Oils Waxes), 131-57 (abstracted at Chem. Abstracts vol. 117:198199x).
Das, T. N., Atmos. Environ., Part A 1992, 26A(15), 3853-7 (abstracted at Chem. Abstracts vol. 117:263861y (1992)).
Chemical Abstracts 119:115286j (1988).
Chemical Abstracts 108:155704e (1988).
Chemical Abstracts 101:96725t.
Chemical Abstracts 98:166121p (1983).
Chemical Abstracts 119:124798m (1993).

*Primary Examiner*—James H. Reamer
*Attorney, Agent, or Firm*—Arthur L. Liberman

[57] ABSTRACT

A process for producing flavor and fragrance compositions by means of first quantitatively and qualitatively substantially continuously analyzing the aroma emitted and rates of emission of the components thereof:
(i) from within the pith section and/or the inner wood section; and
(ii) the outer bark surface of
a living tree, simultaneously, and, optionally from within and from the outer surface of one or more fruits borne by said devices connected to the outer tree trunk surface and an inner location within the tree and, if desired, connected to the fruit surface and an internal location within the fruit and then providing at least the major aroma components found in at least one of the analyses and admixing the resulting components to form a fragrance composition and/or a flavor composition. The living tree, for example, may be a living Douglas Fir or a living Maple Tree or a living Papaya Tree or a living Mahogany Tree or a living Nectarine Tree.

3 Claims, 7 Drawing Sheets

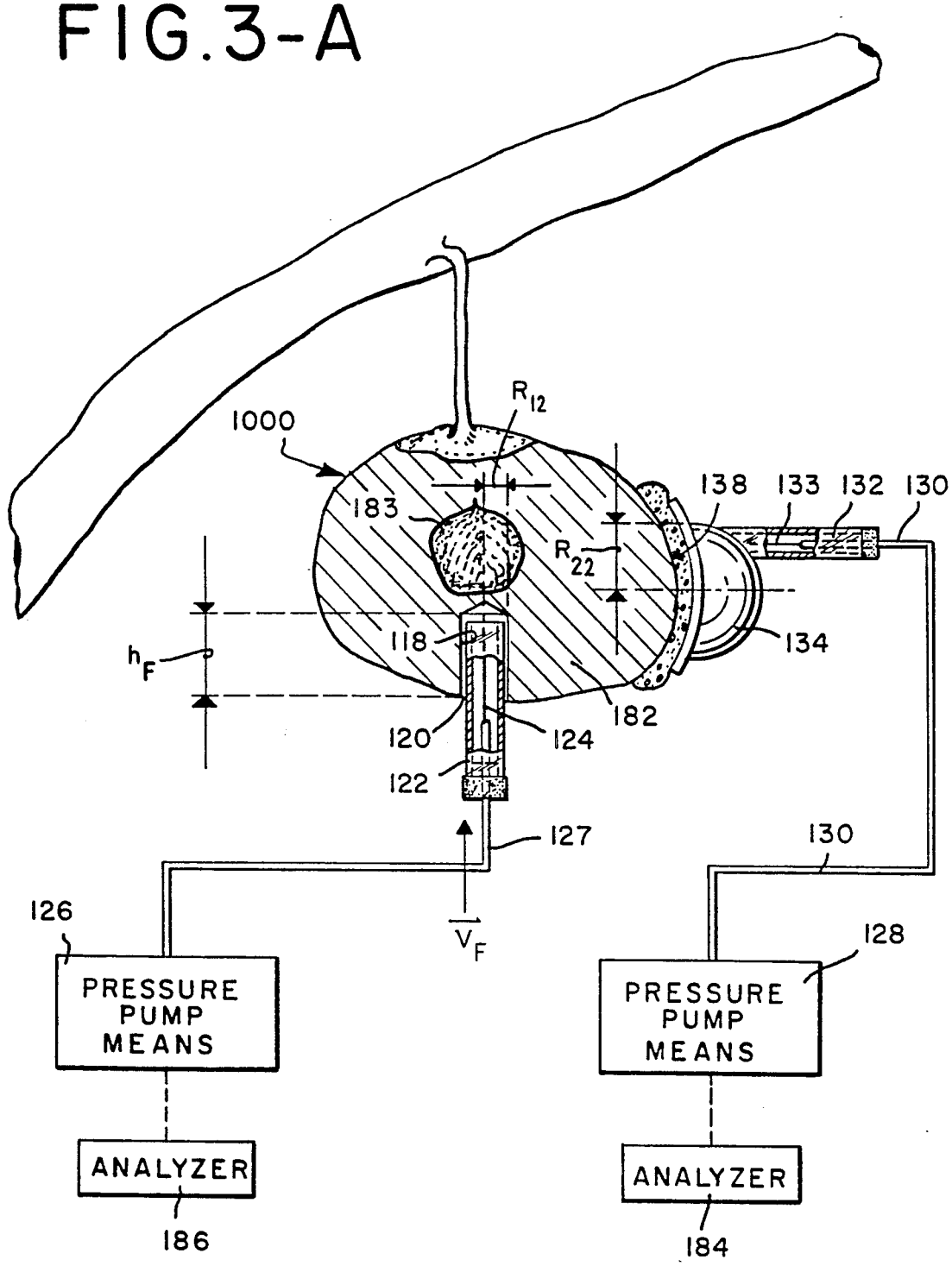
FIG.3-A

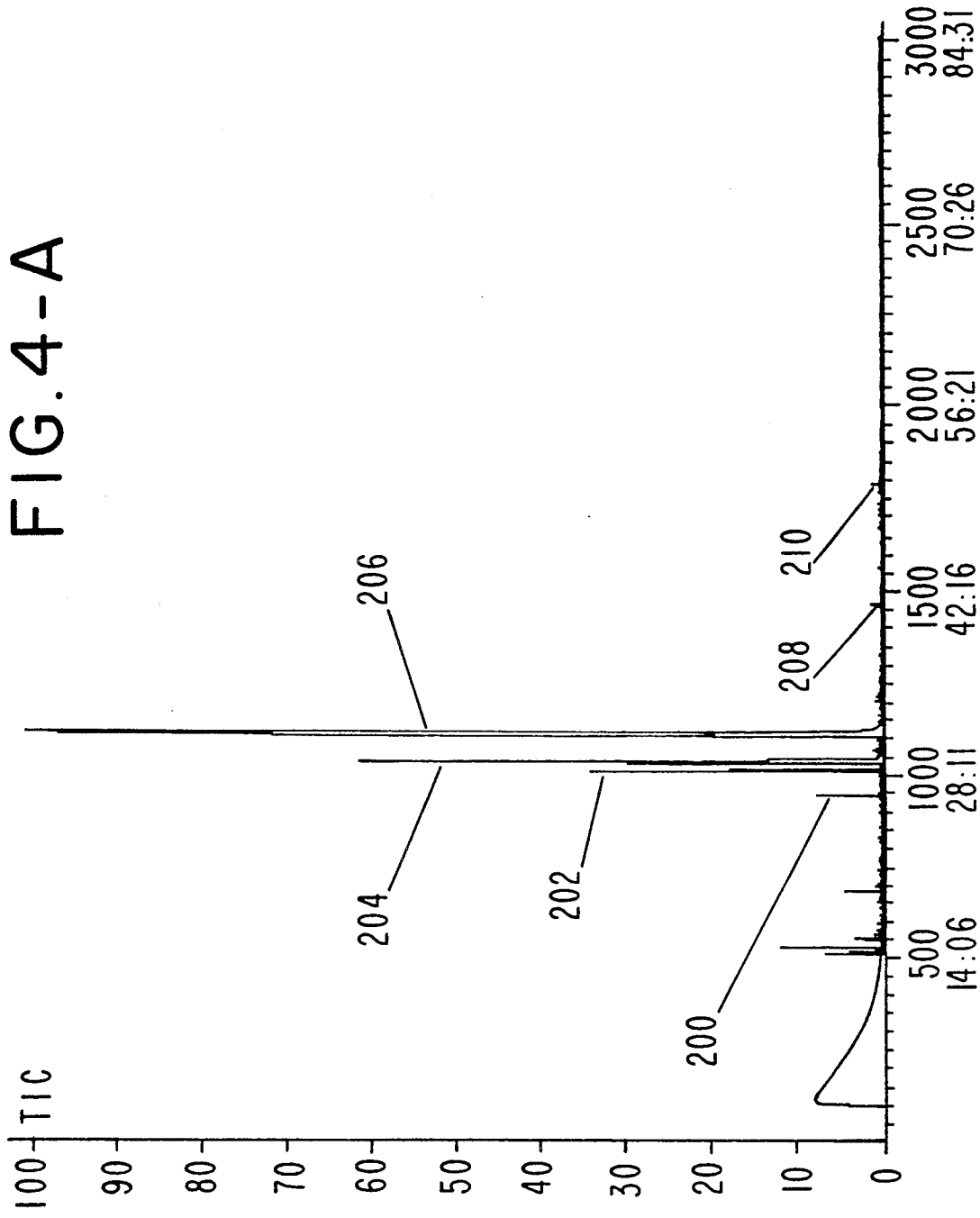

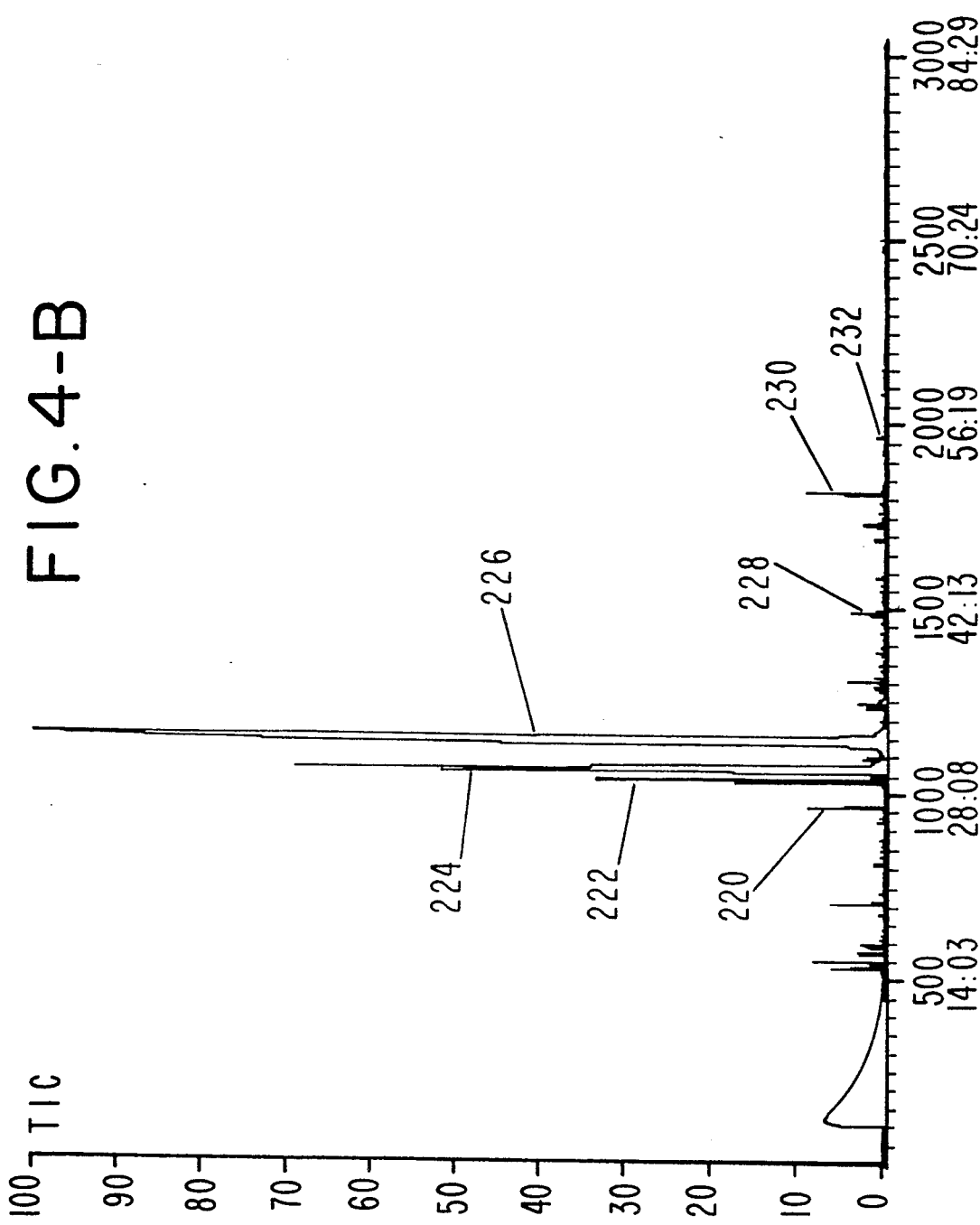
FIG. 4-B

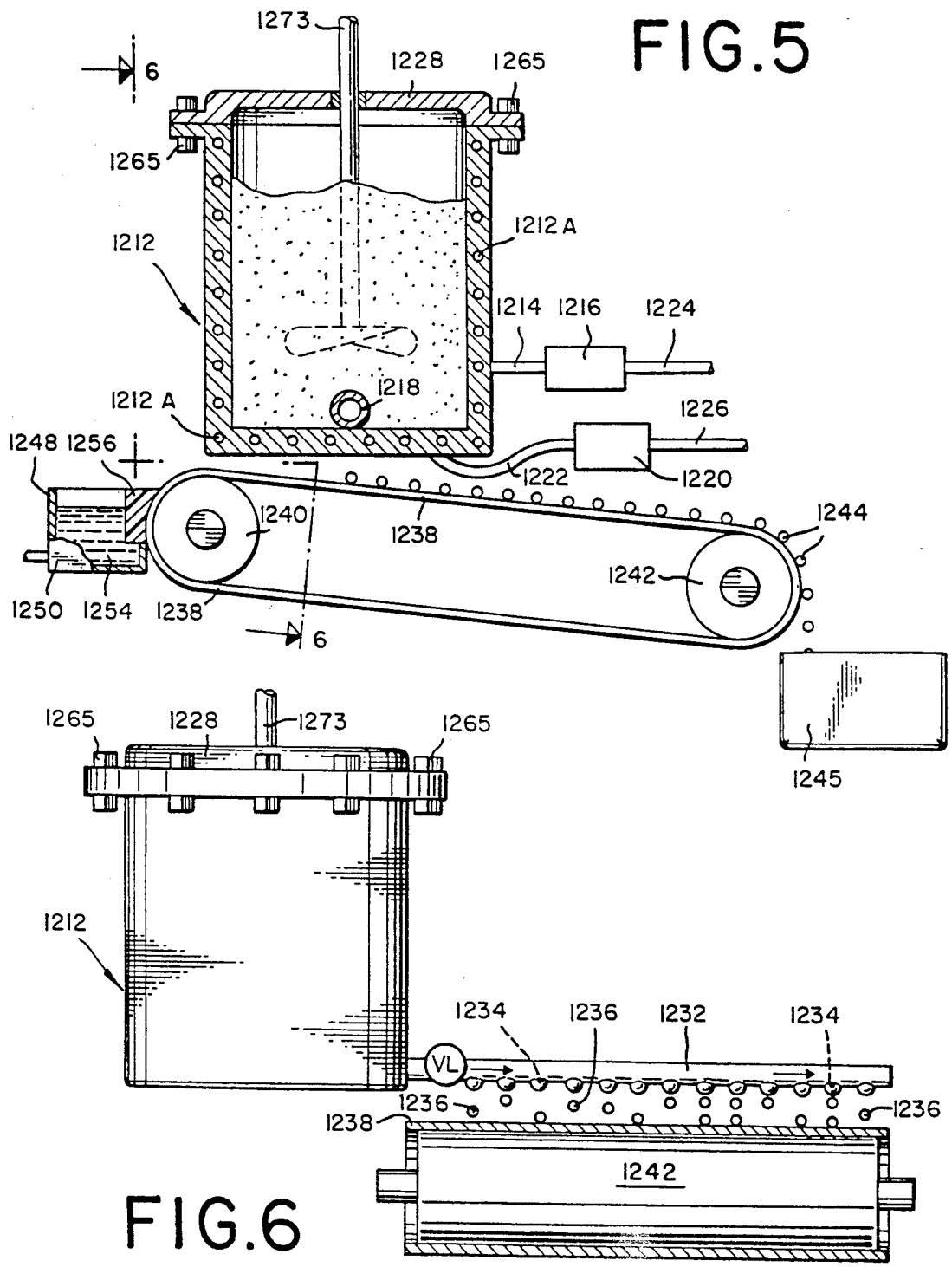

FLAVOR AND FRAGRANCE COMPOSITIONS PRODUCED USING PROCESS FOR QUANTITATIVELY AND QUALITATIVELY SUBSTANTIALLY CONTINUOUSLY ANALYZING THE AROMA EMITTED FROM A LIVING FRUIT

RELATED PATENT APPLICATIONS

This application is a continuation-in-part of application for U.S. patent Ser. No. 023,960 filed on Feb. 26, 1993, now U.S. Pat. No. 5,263,359 issued on Nov. 23, 1993, which, in turn, is a continuation-in-part of application for U.S. patent Ser. No. 988,337 filed on Dec. 9, 1992, now U.S. Pat. No. 5,269,169 issued on Dec. 14, 1993.

BACKGROUND OF THE INVENTION

Our invention concerns a process for producing flavor and fragrance compositions by means of first quantitatively and qualitatively substantially continuously analyzing the aroma emitted and rates of emission of the components thereof from within the inner wood section and/or the pith section and from the outer tree bark surface of a living tree simultaneously, and, optionally, from within and from the outer surface of one or more fruits borne by said living tree, simultaneously, and then providing at least the major aroma components found in at least one of the analyses and admixing the resulting components to form a fragrance composition and/or a flavor composition.

Uses of aromas evolved from the wood parts and the pith sections of living trees as well as living fruits borne by such living trees are highly sought after in the perfumery and flavor arts. Great difficulty has been experienced in attempting to capture and reproduce actual aroma ingredients of the wood parts and pith parts of the living tree as well as living fruits borne by such living trees at various points in time relevant to the maturation of the living tree.

U.S. Pat. No. 5,136,805 issued on Aug. 11, 1992 describes an air-tight flexible transparent container containing at least one living flower immersed in an aqueous suspension. Described in U.S. Pat. No. 5,136,805 is an article useful (i) for display purposes; and/or (ii) for analysis of the headspace in the container above the living flower when the container is fitted with a tube effecting communication of the internal 3-space (internal volume) of the container with outside analytical means and/or (iii) for aromatizing the environment surrounding the container when the container is fitted with a wick effecting communication of the internal 3-space (internal volume) of the container with the environment surrounding the container. However, U.S. Pat. No. 5,136,805 does not teach or infer a technique for quantitatively and qualitatively substantially continuously analyzing the aroma emitted and rates of emission of the components thereof from within and from the outer bark surface of the woody or pithy parts of a living tree simultaneously, and optionally, from within and from the outer surface of one or more fruits borne by said living tree simultaneously.

SUMMARY OF THE INVENTION

Our invention is drawn to a process for producing flavor and fragrance compositions by means of first quantitatively and qualitatively substantially continuously analyzing the aroma emitted and rates of emission of the components thereof:
  (i) from within the inner wood section and/or pith section; and
  (ii) from the outer tree bark surface of
one or more woody parts of a living tree simultaneously, and, optionally, quantitatively and qualitatively substantially continuously analyzing the aroma emitted and rates of emission of the components thereof:
  (i') from within; and
  (ii') from the outer surface of
one or more living fruits borne by said living tree and then providing at least the major aroma components found in at least one of the analyses and admixing the resulting components to form a fragrance composition and/or a flavor composition.

Examples of such living trees are living Douglas Fir, living Texas Cedarwood trees, living Virginia Cedarwood trees, living Cherry trees, living Mahogany trees, living Nectarine trees, living Papaya trees, and living Maple trees. Examples of living Nectarine trees are those such as the Red Jewel Nectarine tree (disclosed and claimed in U.S. Pat. No. P.P. 8,013 issued on Oct. 27, 1992) and the Red Diamond Nectarine tree (disclosed and claimed in U.S. Pat. No. P.P. 3,165). The specifications of U.S. Pat. Nos. P.P. 3,165 and 8,013 are incorporated by reference herein.

Our process comprises the steps of:
  (a) removing a cylindrical core section from a section of one or more wood parts and/or the pith part of the living tree to form one or more core voids;
  (b) placing a first trapping tube (connected to a vacuum pump) into the core void(s);
  (c) applying an enclosure containing a second trapping tube (connected to a vacuum pump) to a portion of unbroken tree bark surface of the same living tree in a sealably affixable manner;
  (d) engaging both vacuum pumps; and
  (e) analyzing the substances trapped in the trapping tubes on a substantially continuous basis; and, optionally:
  (a') removing a cylindrical core section from a section of one or more living fruits borne by said living tree to form one or more core voids;
  (b') placing a third trapping tube (connected to a vacuum pump) into the core void(s);
  (c') applying an enclosure containing a fourth trapping tube (connected to a vacuum pump) to a portion of unbroken surface of the same living fruit in a sealably affixable manner;
  (d') engaging both vacuum pumps; and
  (e') analyzing the substances trapped in the trapping tubes on a substantially continuous basis;
and then
  (a") providing from at least one independent source at least the major aroma components found in at least one of the two analyses of steps (e) and/or (e'); and
  (b") admixing the resulting components to form a perfume composition and/or a flavor composition.

Thus, our invention also contemplates the use of multiple ongoing simultaneous analysis of (a) the inner and outer sections of a living tree and (b) the inner and outer sections of living fruit growing on said living tree (as is the case of a nectarine growing on a nectarine tree) according to the process disclosed and claimed in copending application for U.S. patent Ser. No. 988,337 filed on Dec. 9, 1992 the specification for which is incorporated herein by reference.

DETAILED DESCRIPTION OF THE INVENTION

Our invention covers a process for producing flavor and fragrance compositions by means of first quantitatively and qualitatively substantially continuously analyzing the aroma emmited and rates of emission of the components thereof:

(i) from within the inner wood section and/or pith section; and (ii) from the outer tree bark surface of one or more wood parts (e.g., the main trunk) of a living tree simultaneously, and, optionally, quantitatively and qualitatively substantially continuously analyzing the aroma emmited and rates of emission of the components thereof:

(i') from within; and (ii') from the outer surface of one or more living fruits borne by said living tree simultaneously, and then providing at least the major aroma components found in at least one of the analyses and admixing the resulting components to form a fragrance composition and/or a flavor composition, consisting essentially of the steps of:

(a) providing a living tree located on a given central axis having an outer tree bark surface, a substantial portion of which is located at a given distance from the central trunk or tree limb axis and an inner volume including an inner heartwood section or an inner sapwood section and in a number of instances an inner pith volume surrounding said central axis and encompassed by said outer tree bark surface;

(b) removing a depth core section from said inner volume running from said outer tree bark surface to a depth of from about halfway up to entirely to the central trunk or tree limb axis, into said inner volume along a directional vector extending substantially radially from said central axis to said outer tree bark surface within said inner volume;

(c)-1 providing first analytical apparatus means comprising a first trapping tube means attached to first negative pressure pump means associated with first chemical analysis means (e.g., GC-mass spectral, nuclear magnetic resonance, Raman spectral and infrared analytical equipment);

(c)-2 providing second analytical apparatus means second negative pressure pump means associated with second chemical analysis means;

(d) providing a hollow flexible enclosure means (e.g., a spherical cup-like enclosure) having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer tree bark surface of said living tree at said enclosure rim means;

(e) causing said enclosure means to sealably grip said portion of said outer tree bark surface of said living tree at said enclosure rim means;

(f) inserting said first trapping tube means into said core section void along said directional vector;

(g) inserting said second trapping tube means through said insertion orifice causing it to be extended into said enclosure means void;

(h) simultaneously engaging said first negative pressure pump means and said second pressure pump means whereby components of the aroma evolving from said outer tree bark surface of said living tree are entrapped in said second trapping tube means and components of the aroma evolving from within the pith and/or wood section of said living tree are entrapped in said first trapping tube means, simultaneously; and (j) analyzing the contents of said first trapping tube means using said first chemical analysis means and said second trapping tube means using said second chemical analysis means substantially continuously and substantially simultaneously; and optionally, simultaneously:

(a') providing one or more living fruits borne by said living tree each of which fruits is located on a given central axis having an outer surface, a substantial portion of which is located at a given distance from the central axis and an inner volume surrounding said central axis and encompassed by said outer surface;

(b') removing a depth core section from said inner volume running from said outer surface to a depth of from about halfway up to entirely to the central axis into said inner volume along a directional vector extending substantially radially from said central axis to said outer surface within said inner volume;

(c)-1: providing third analytical apparatus means comprising a third trapping tube means attached to third negative pressure pump means associated with third chemical analysis means (e.g, GC-mass spectral, nuclear magnetic resonance, Ramon spectral and infrared analytical equipment);

(c)-2: providing fourth analytical apparatus means comprising a fourth trapping tube means attached to fourth negative pressure pump means associated with fourth chemical analysis means;

(d') providing a hollow flexible enclosure means (e.g., a spherical cup-like enclosure) having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer surface of said living fruit at said enclosure rim means;

(e') causing said enclosure means to sealably grip said portion of said outer surface of said living fruit at said enclosure rim means;

(f') inserting said third trapping tube means into said core section void along said directional vector;

(g') inserting said fourth trapping tube means through said insertion orifice causing it to be extended into said enclosure means void;

(h') simultaneously engaging said third negative pressure pump means and said fourth negative pressure pump means whereby components of the aroma evolving from said outer surface of said living fruit are entrapped in said fourth trapping tube means and components of the aroma evolving from within said living fruit are entrapped in said third trapping tube means, simultaneously;

(j') analyzing the contents of said third trapping tube means using said third chemical analysis means and said fourth trapping tube means using said fourth chemical analysis means substantially continuously and substantially simultaneously;

and then (a'') providing from at least one independent source at least the major aroma components found in at least one of the two analyses of steps (j) and (j'); and (b'') admixing the resulting components to form a perfume composition and/or a flavor composition.

Examples of various trees both fruit bearing and non-fruit bearing which are the subjects of our invention are as follows:

(i) the Douglas Fir (*Psoudotsuga taxifolia* (Lamb.) Britt;
(ii) the Papaya tree (*Carica papaya*);
(iii) the Coconut Palm tree (*Cocos nucifera*);
(iv) the Texas Cedarwood (*Thuja plicata*);
(v) the Mahogany tree (*Swietenia candollea*);
(vi) the Wild Guyana Sandalwood tree;
(vii) the East Indian Sandalwood tree;
(viii) the Nectarine tree (the Red Jewel Nectarine tree and the Red Diamond Nectarine tree).

Thus, for example, in the case of a living Douglas Fir tree having an average trunk outside diameter of 8", the depth core would be about ¼" in diameter and the tube entering the core containing trapping material would be approximately 3/16" in diameter and about 4" in length. Enclosed within the surrounding tube would be a trap such as a TENAX ® trap which would be ⅛" in diameter and 3.5" in length, for example.

When carrying out our process involving a living tree and one or more living fruits borne by said living tree, when the living fruit is one that has a pit such as a peach or a nectarine or a plum, then obviously the depth core can only extend to the outer surface of the pit and preferably the depth core (with respect to the living fruit) should extend about two-thirds of the way into the fruit without touching the surface of the pit. Thus, for example, in the case of a nectarine the depth core would be about a ¼" in diameter and the tube entering the core containing the trapping material would be approximately 3/16" in diameter and about 0.75" in length. Enclosed within the surrounding tube would be a trap such as a TENAX ® trap which would be ⅛" in diameter and 0.7" in length, for example.

Thus, various trapping materials are useful in the practice of our invention in both the trap used in trapping the materials emitted from within the inner wood section and/or pith section of the living tree and entrapping the materials emitted from the outer tree bark surface of the living tree. As stated, supra, TENAX ® is a preferable material. Various forms of TENAX ® are useful, for example, TENAX ®-GC. TENAX ® is a registered trademark of ENKA N.V. of The Kingdom of The Netherlands (CAS Registration No. 24938-68-9). Various forms of TENAX ® and methods of producing such forms of TENAX ® are described in the following U.S. patent the disclosures of which are incorporated herein by reference:

U.S. Pat. No. 3,400,100 issued on Sep. 3, 1968 ("Process For The Preparation Of Polyphenylene Ethers")

U.S. Pat. No. 3,644,227 issued on Feb. 22, 1972 ("Separation Of Poly(2,6-Dimethyl-1,4-Phenyleneoxide) from its blends with other polymers")

U.S. Pat. No. 3,703,564 issued on Nov. 21, 1972 ("Bis[Polyphenyleneoxide]-Ester Block Copolymers")

U.S. Pat. No. 4,431,779 issued on Feb. 14, 1984 ("Polyetheramide-Polyphenylene Ether Blends")

U.S. Pat. No. 4,801,645 issued on Jan. 31, 1989 ("Thermoplastic Resin Composition")

TENAX ®-GC is actually a polyphenyleneoxide defined according to the structure:

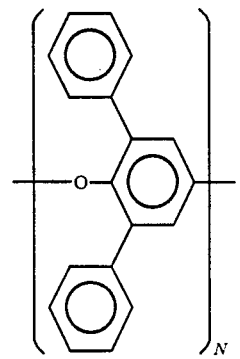

wherein N is an integer of from about 100 up to about 150.

Other trapping materials useful in the practice of our invention are as follows: Activated Carbon marketed by Aldrich Chemical Company of 1001 West Saint Paul Avenue, Milwaukee, Wis. 53233 (Catalog Nos. 16, 155-1; 29, 259-1; 24, 223-3; 24, 224-1 and 24, 227-6); Activated Alumina marketed by Sigma Chemical Company of St. Louis, Missouri (Catalog Nos. A8753; A8878; A9003; A1772; A1522 and A2272); Silica Gels marketed by Sigma Chemical Company, for example, Catalog Nos. S4004; S6628 and H8506; CHROMOSORB ® (registered trademark of the Johns-Manville Company of Manville, N.J.) such as CHROMOSORB ® such as LC-1; CHROMOSORB ® LC-2; CHROMOSORB ® LC-3, and CHROMOSORB ® LC-7 marketed by the Sigma Chemical Company under Catalog Nos. C 0641; C 0766, C 5517 and C 6269.

The negative pressure pump means of our invention is preferably a vacuum pump of the "Low Flow" variety, for example, "Low Flow" pumps marketed by the Ametek Company of Largo, Fla. 34643 (the Ametek Constant Flow Sampler).

Examples of other trees amenable to the practice of our invention are as follows:

(i) the Green Ash Tree named "Cimmzam" disclosed and claimed in U.S. Pat. No. P.P. 8,077, granted on Dec. 29, 1992 (the specification for which is incorporated herein by reference);

(ii) the Prima Black Plum 5-25 Tree disclosed and claimed in U.S. Pat. No. P.P. 8,067 granted on Dec. 22, 1992 (the specification for which is incorporated herein by reference);

(iii) the Prima Black Plum 8-15 Tree disclosed and claimed in U.S. Pat. No. P.P. 8,068 granted on Dec. 22, 1992 (the specification for which is incorporated herein by reference);

(iv) the Plum Tree "Green Jade" disclosed and claimed in U.S. Pat. No. P.P. 8,069 granted on Dec.

22, 1992, (the specification for which is incorporated herein by reference);

(v) the Peach Tree "Summer Sweet" disclosed and claimed in U.S. Pat. No. P.P. 8,070 granted on Dec. 22, 1992, (the specification for which is incorporated herein by reference); and (vi) the Peach Tree "Compact Flavorette" disclosed and claimed in U.S. Pat. No. 8,071 granted on Dec. 22, 1992, (the specification for which is incorporated herein by reference).

At least one of the living tree/fruit fragrance compositions produced according to the process of our invention and one or more auxiliary perfume ingredients including, for example, alcohols, aldehydes, nitriles, esters, cyclic esters, ketones, ethers, synthetic essential oils and natural essential oils may be admixed so that the combined odors of the individual components produce a pleasant and desired fragrance particularly and preferably in the green, herbaceous, fruity and floral fragrance area.

By the term "tree/fruit fragrance compositions" is meant a fragrance composition produced by admixing the major aroma components found in at least one of the two analyses of steps (j) and (j') defined, supra.

Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to its particular olfactory characteristics, but the overall effect of the perfume composition will be the sum of the effects of each of the ingredients. Thus, one or more of the living tree/fruit fragrance compositions of our invention and one or more auxiliary perfume ingredients can be used to alter the aroma characteristics of a perfume composition, for example, by utilizing or moderating the olfactory reaction contributed by at least one other ingredient in the composition.

The amount of at least one of the living tree/fruit fragrance compositions of our invention useful in perfume compositions for augmenting or enhancing of floral, fruity, magnolia, and jasmine aromas may vary from about 1% by weight of the perfume composition up to 100% by weight of the perfume composition (the entire composition can be composed of the living tree/fruit fragrance components determined by the practice of our invention).

At least one of the living tree/fruit compositions of our invention and, if desired, one or more auxiliary perfume ingredients can be used to impart green, herbaceous, fruity and lactonic aroma nuances, topnotes and undertones to soaps, anionic, cationic, nonionic or zwitterionic detergents, fabric softener compositions, fabric softener articles, cosmetic powders, hair preparations and the like. The amount employed can range up to 100% by weight of the fragrance components and can range up to approximately 0.5% of the weight of the perfumed article and will depend upon considerations of cost, nature of the end product, the effect desired on the finished product and the particular fragrance sought.

At least one of the living tree/fruit fragrance compositions of our invention and, if desired, one or more auxiliary perfume ingredients are useful, taken alone or in perfume compositions as olfactory components in anionic, cationic, nonionic or zwitterionic detergents, soaps, fabric softener compositions, fabric softener articles for use in clothes dryers (e.g., "BOUNCE®", a registered trademark of the Procter & Gamble Company of Cincinnati, Ohio), space odorants and deodorants, perfumes, colognes, toilet waters, bath preparations, such as lacquers, brilliantines, creams, deodorants, hand lotions and sun screens; powders such as talcs, dusting powders, face powders and the like.

When used as an olfactory component in perfume compositions or perfumed articles, such as anionic, cationic, nonionic, or zwitterionic detergents and fabric softener compositions and fabric softener articles (e.g., for use in clothing dryers) as little as 0.05% of at least one of the living tree/fruit fragrance compositions of our invention and, if desired, one or more auxiliary perfume ingredients will suffice to impart various green, herbaceous, fruity and lactonic aroma nuances. Generally, no more than 0.05% of at least one of the living tree/fruit perfume compositions of our invention and, if desired, one or more auxiliary perfume ingredients based on the ultimate end product is required in the perfumed article.

In addition, the perfume composition or fragrance composition of our invention can contain a vehicle or carrier for at least one of the living tree/fruit perfume compositions of our invention and, if desired, one or more auxiliary perfume ingredients. The vehicle can be a liquid such as a non-toxic alcohol, a non-toxic glycol or the like. The carrier can also be an absorbent solid, such as a gum (e.g., gum arabic, xanthan gum or guar gum) or components for encapsulating the composition (such as gelatin as by means of coacervation).

When the living tree/fruit compositions of our invention are used as food flavor adjuvants, or are used to augment or enhance the flavor or aroma characteristics of foodstuffs, the nature of the co-ingredients included with said living tree/fruit compositions in formulating the product composition will also serve to augment the organoleptic characteristics of the ultimate foodstuff treated therewith.

As used herein in regard to flavors, the term "augment" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

As used herein in regard to food flavors, the term "enhance" is used herein to mean the intensification of a flavor or aroma characteristic or note without the modification of the quality thereof. Thus, "enhancement" of a flavor or aroma means that the enhancement agent does not add any additional flavor note.

As used herein the term "foodstuff" includes both solids and liquids, and ingestible materials or chewable but non-ingestible materials such as chewing gum. Such materials usually do, but need not, have nutritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with the living tree/- fruit compositions non-reactive with the living tree/fruit compositions of our invention and "ingestibly" acceptable and thus non-toxic or otherwise non-deleterious, nothing particularly critical resides in the selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium, peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes, yeast foods, e.g., calcium lactate and calcium sulfate; nitrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta,beta-dimethyl- acrolein, n-hexanal, 2-hexenal, cis-3-hexenal, 2-heptanal, 4-(p-hydroxyphenyl)-2-butanone, alpha-ionone, beta-ionone, methyl-3-butanone, 2-pentanone, 2-pentenal and propanal; alcohols such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, Bulgarian rose, yara, yara, natural raspberry oil and vanilla; lactones; sulfides, e.g., methyl sulfide and other materials such as maltol, pulegone mercaptan, alpha-phellandrene, ethyl maltol, 2,2,4,4,6,6-hexamethyl-S-trithiane, acetoin and acetals, (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the living tree/fruit compositions can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of living tree/fruit compositions employed in a particular instance can vary over a relatively wide range whereby to its desired organoleptic effects having reference to the nature of the product are achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter the organoleptic characteristics of the parent composition, whether foodstuff per se or flavoring composition.

The use of insufficient quantities of living tree/fruit compositions will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of living tree/fruit compositions ranging from a small but effective amount, e.g., about 0.1 parts per million up to about 50 parts per million by weight based on total composition (more preferably, from about 0.2 ppm up to about 10 ppm) are suitable. Concentrations in excess of the maximum quantity stated are not normally recommended, since they fail to prove commensurate enhancement of organoleptic properties. In those instances, wherein the living tree/fruit compositions are added to the foodstuff as an integral component of a flavoring composition, it is, of course, essential that the total quantity of flavoring composition employed be sufficient to yield an effective living tree/fruit composition concentration in the foodstuff product.

Food flavoring compositions prepared in accordance with the present invention preferably contain the living tree/fruit composition concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistence, homogeneity of dispersion, etc. Alternatively, flavoring compositions in the form of particulate solids can be conveniently prepared by mixing the living tree/fruit compositions with, for example, gum arabic, gum tragacanth, carageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and living tree/fruit compositions in a dry blender until the requisite degree of uniformity is achieved.

It is presently preferred to combine with the living tree/fruit compositions the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;
Gamma-undecalactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene);
2-(4-hydroxy-4-methylpentyl) norbornadiene prepared according to U.S. appliation for U.S. Pat. No. 461,703 filed on Apr. 17, 1974, now U.S. Pat. No. 3,886,289.
Natural blackcurrant juice;
Buchu lead oil;
alpha-phellandrene;
Cis-3-hexen-1-ol;
Terpinenol-4;
Ethyl maltol;
Methyl benzoate;
Benzaldehyde;
Coriander oil;
Alpha-ionone;
Ethyl heptanoate;
Methyl anthranilate;
Ethyl anthranilate;
Cinnamic alcohol;
Amyl valerinate;
Cinnamyl propionate;
Rhodinyl acetate;
Methyl Beta-hydroxy butyrate;
Ethyl Beta-hydroxy butyrate;
2-Phenyl-3-carboethoxyfuran;
Cyclohexyl disulfide;
Grapefruit oil;
Nootkatone;
Bergamot oil;
Citral;
Amyl alochol;
5-Phenyl-4-pentenal;
5-Phenyl-2-pentenal;
Allyl caproate;
2-(n-pentyl) thiazole;
2-(i-butyl) thiazole;
2-(i-propyl) thiazole;
2-(n-propyl) thiazole;
2-Phenyl-4-pentenal;
2-Phenyl-4-pentenaldimethylacetal;
Methional;
4-Methylthiobutanal;
2-Ethyl-3-acetylpyrazine;
Tetramethyl pyrazine;
2-Methyl pyrazine;
Trans-2-hexenal;
Hydrolyzed vegetable protein;
Monosodium glutamate;
Dimethyl disulfide;
Methyl propyl disulfide;
Methyl propenyl disulfide;
Methyl allyl disulfide;
Allyl propyl disulfide;
Propyl propenyl disulfide;
Dipropyl disulfide;
Diallyl disulfide;
Propyl propenyl trisulfide;
Thiopropanal-S-oxide;
Thiobutanal-S-oxide;
Thioethanal-S-oxide;
Thiohexanal-S-oxide; and
Propyl propene thiosulfonate.

It will thus be apparent that at least one of the living tree/fruit compositions of our invention and, if desired, one or more auxiliary perfume or flavor ingredients can be used to alter the sensory properties, particularly organoleptic properties of a wide variety of consumable materials.

(i) from within; and (ii) from the outer tree bark surface of the living tree simultaneously.

Figure 3:
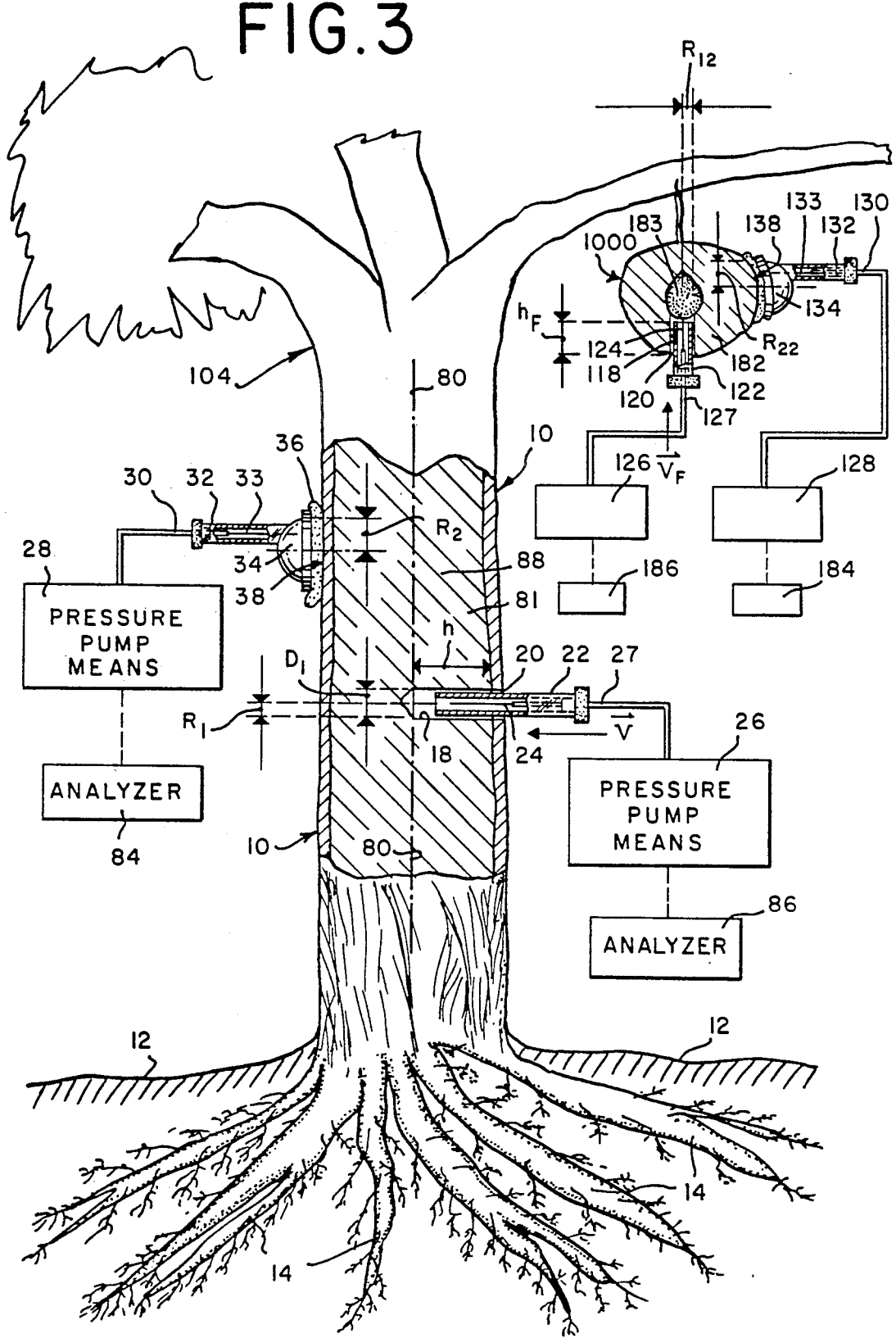

FIG. 3 is a schematic drawing showing a cut-away side elevation view of the wood part of a living tree bearing living fruit being quantitatively and qualitatively substantially continuously analyzed for the aroma emitted and rate of emission of the components thereof:

(i) from within; and (ii) from the outer tree bark surface of the living tree and, simultaneously:

(i') from within; and (ii') from the outer surface of the living fruit borne on said living tree simultaneously.

FIG. 3A is a detailed schematic drawing showing a cut-away side elevation view of a living fruit borne on the living tree of FIG. 3, said living fruit being quantitatively and qualitatively substantially continuously analyzed for the aroma emitted and rate of emission of the components thereof:

(i) from within; and (ii) from the outer surface of the living fruit simultaneously.

Figure 2:
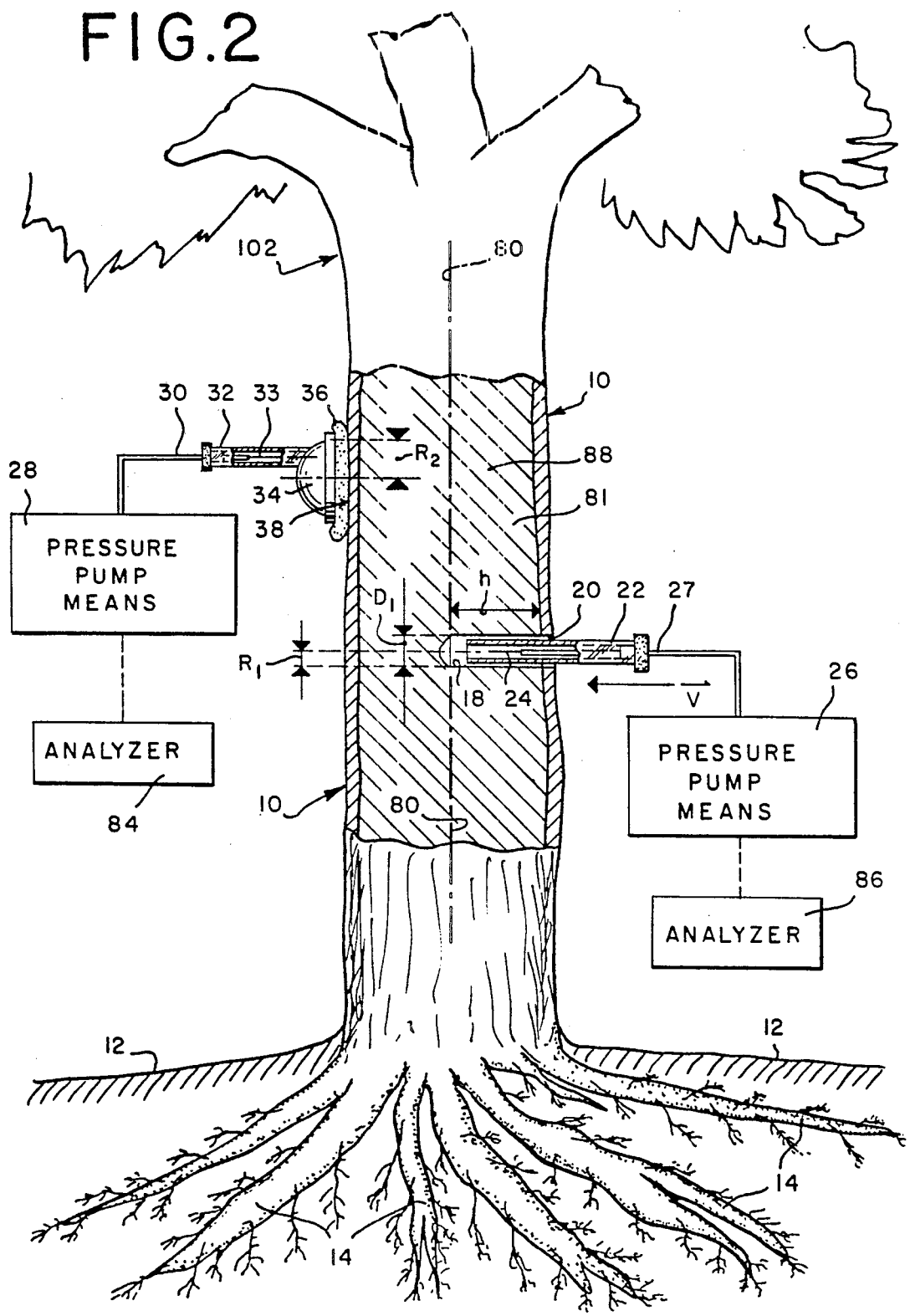
FIG. 2 is a schematic drawing showing a cut-away side elevation view of the wood part (without the presence of a pith section) of a living tree (without bearing any living fruit) being quantitatively and qualitatively substantially continuously analyzed for the aroma emitted and rate of emission of the components thereof.

FIG. 4A is the GC mass spectrum of the composition of the aroma produced by carrying out Example I, infra, of the interior of a living Douglas Fir tree using the apparatus of FIG. 2.

FIG. 4B is the GC mass spectrum of the aroma emitted from the external surface of a living Douglas Fir tree in Example I, infra, using the apparatus shown in FIG. 2.

FIG. 5 represents a cut-away side elevation view of apparatus used in forming perfumed polymers containing at least one of the living tree/fruit compositions of our invention.

FIG. 6 is a front view of the apparatus of FIG. 5 looking in the direction of the arrows.

DETAILED DESCRIPTION OF THE DRAWINGS

Figure 1:
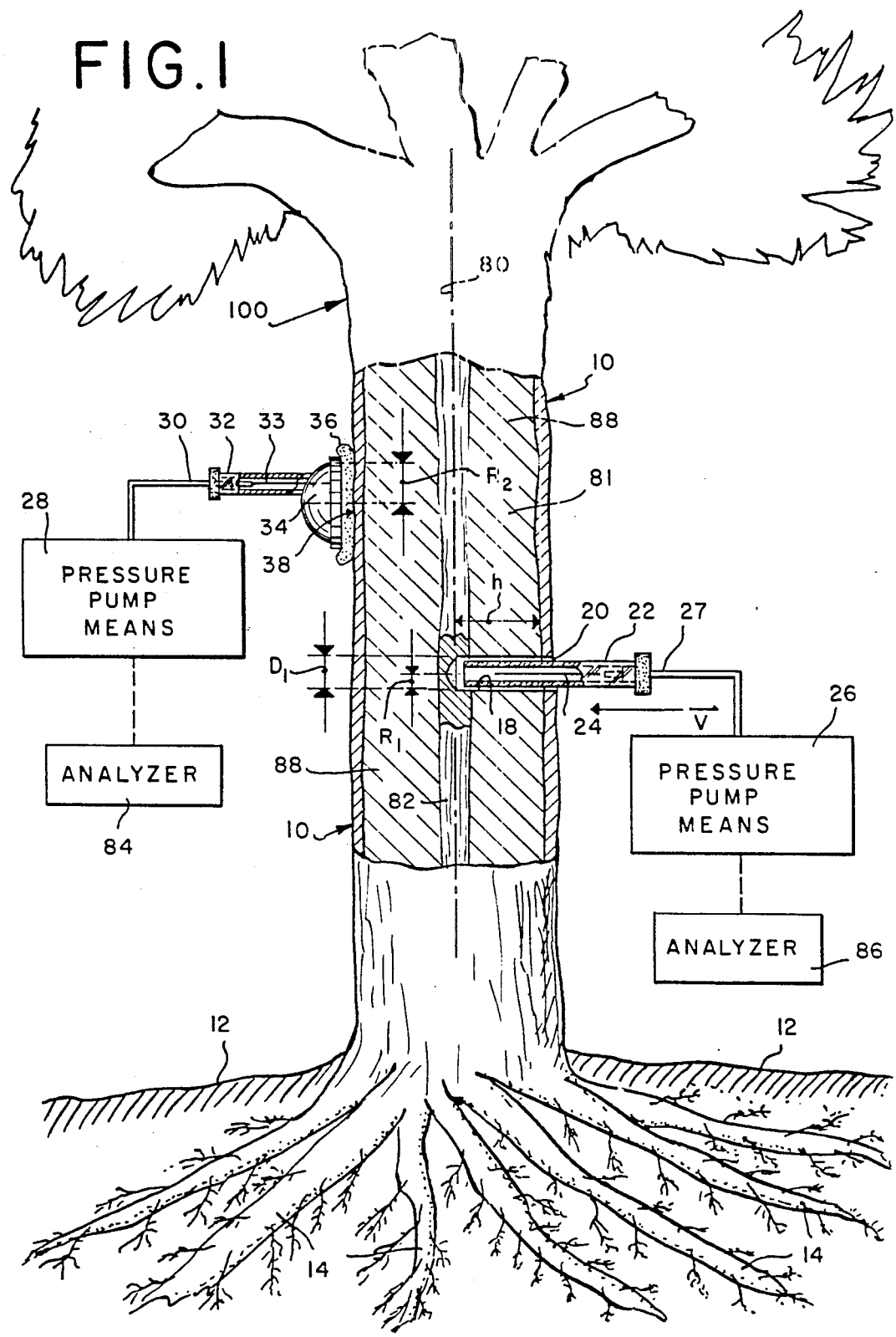
FIG. 1 is a schematic drawing showing a cut-away side elevation view of the wood and pith portions of a living tree (without bearing any living fruit) being quantitatively and qualitatively substantially continuously analyzed for the aroma emitted and rate of emission of the components thereof:
(i) from within; and
(ii) from the outer tree bark surface
of the living tree simultaneously.

Referring to FIG. 1, a living tree having its axis 80 and roots 14 living in ground 12 having an inner volume 81, inner wood volume 88 and pith volume 82 and a tree bark surface 10 is shown having the aroma and rate of emission of the components thereof:

(i) from within the inner pith section of the living tree; and (ii) from the outer tree bark surface of the living tree being analyzed simultaneously.

A substantial portion of the outer tree bark surface 10 is located at a given distance "h" (e.g., 4") from the central axis 80, and an inner pith volume 82 surrounds the central axis 80 and is encompassed by the wood section 88 surrounding the pith volume 82 and outer surface 10; and a depth core section 18 is removed from the inner volume 81 including part of the inner wood volume 88 and pith volume 82 along a directional vector "V" extending substantially radially from the central axis 80 to the outer tree bark surface 10 within the inner volume 81 including the pith volume 82. The depth core section 18 has an effective diameter $D_1$ (e.g., about $\frac{1}{4}$") equal to 2×(the effective radius, $R_1$ (about $\frac{1}{8}$")) and a core section volume ranging from about $$[\pi R_1^2 h]$$

down to about $$\left[\frac{\pi R_1^2 h}{2}\right]$$

thereby forming a core section void within the living tree. First analytical apparatus means in FIG. 1 comprises a first trapping tube means (22, 24) which is a glass outer tube 22 and a trapping tube 24 inserted through opening 20 into depth core 18. Attached to the trapping tube 24 (which may, for example, contain TENAX ®-GC) is tube 27 connected to a negative pressure pump means 26 ("first negative pressure pump means"). Reference numeral 86 represents analytical apparatus capable of providing GC-mass spectra of the trapped substance which may be taken further together with spectral apparatus capable of providing infrared spectra of the trapped substance, spectral apparatus capable of providing NMR spectra of the trapped substance and spectral apparatus capable of providing Raman spectra of the trapped substance. The analytical apparatus represented by reference numeral 86 is also herein referred to as "first analyzer means".

Second analytical apparatus means for analyzing the aroma emitted from the tree bark surface of the living tree of FIG. 1 comprises second trapping tube means 32–33 (outer tube 32 encompassing inner trapping tube 33) inserted into enclosure 34 which is sealably affixed at 36 to a portion of the tree bark surface 38 of the living tree 100. The trapping tube means is connected to tube 30 which is connected to negative pressure pump 28 ("second negative pressure pump means") associated with analyzer 84 ("second analyzer means") (e.g., GC-mass spectral analyzer; Raman spectral analyzer; nuclear magnetic resonance analyzer; and infrared analyzer). The apparatus is maintained in place in conjunction with the living tree, e.g., the living tree of FIG. 1. The trapping tube is inserted into the enclosure means (e.g., a hemispherically-shaped cup means having an inner cup means void and an outer cup means surface surrounding the void and terminating at a substantially circular rim of radius $R_2$ with the inner volume of said cup means being about:

$$[\tfrac{2}{3}\pi R_2^3].$$

Thus, when the first negative pressure pump means 26 and the second negative pressure pump means 28 are simultaneously engaged, the components of the aroma evolving from the outer tree bark surface of the living tree (e.g., the living tree shown by reference numeral 100) are entrapped in the second trapping tube means inner trapping tube 33 and the first trapping tube means inner trapping tube 24 simultaneously, enabling the contents of the first trapping tube means 22-24 and the second trapping tube means 32-33 to be continuously analyzed substantially simultaneously using first and second chemical analysis means 86 and 84, respectively.

Referring to FIG. 2, a living tree (e.g., a Douglas Fir) having axis 80 and roots 14 living in ground 12 having an inner volume 81 and inner wood volume 88 and a tree bark surface 10 is shown having the aroma and rate of emission of the components thereof:

(i) from within the inner wood section of the living tree; and (ii) from the outer tree bark surface of the living tree being analyzed simultaneously.

A substantial portion of the outer tree bark surface 10 is located at a given distance "h" (e.g., 4") from the central axis 80 and an inner volume 88 surrounds the central axis 80 and is encompassed by the wood section 88 and the outer tree bark surface 10; and a depth core section 18 is removed from the inner volume 81 including part of the inner wood volume 88 along a directional vector "V" extending substantially radially from the central axis 80 to the outer tree bark surface 10 within the inner volume 81. The depth core section 18 has an effective diameter $D_1$ (e.g., about ¼") equal to $2\times$(the effective radius, $R_1$ (about ⅛")) and a core section volume ranging from about $$[\pi R_1^2 h]$$

down to about $$\left[\frac{\pi R_1^2 h}{2}\right]$$

thereby forming a core section void within the living tree. First analytical apparatus means in FIG. 2 comprises a first trapping tube means (22, 24) which is a glass outer tube 22 and an inner trapping tube 24 inserted through opening 20 into depth core 18. Attached to the trapping tube 24 (which may, for example, contain TENAX ®-GC) is tube 27 connected to a negative pressure pump means 26. Reference numeral 86 represents analytical apparatus capable of providing GC-mass spectra of the trapped substance which may be taken further together with spectral apparatus capable of providing infrared spectra of the trapped substance and spectral apparatus capable of providing NMR spectra of the trapped substance.

Second analytical apparatus means (for analyzing the aroma emitted from the surface of the living tree of FIG. 2) comprises second trapping tube means 32 inserted into enclosure 34 which enclosure is sealably affixed at 36 (with reference numeral 36 indicating an approved non-toxic sealing substance which may, for example, be a high molecular weight alpha,omega-polyoxyethylene glycol) to the portion of the tree bark surface of the living tree 38. The trapping tube means is connected to tube 30 which is connected to negative pressure pump 28 associated with analyzer 84 (e.g., GC-mass spectral analyzer; nuclear magnetic resonance analyzer; and infrared analyzer). The apparatus is maintained in place in conjunction with the living tree, e.g., the living tree of FIG. 2. The trapping tube is inserted into the enclosure means (e.g., a hemispherically-shaped cup means having an inner cup means void and an outer cup means surface surrounding the void and terminating at a substantially circular rim of radius $R_2$ with the inner volume of said cup means being about:

$$[\tfrac{2}{3}\pi R_2^3]$$

Thus, when the first negative pressure pump means 26 and the second negative pressure pump means 28 are simultaneously engaged, components of the aroma evolving from the outer tree bark surface of the living tree (e.g., the living tree shown by reference numeral 102) are entrapped in the second trapping tube means 32 and the first trapping tube means 22 simultaneously, enabling the contents of the first trapping tube means and the second trapping tube means to be continuously analyzed substantially simultaneously using the first and second chemical analysis means 86 and 84, respectively.

Referring to FIGS. 3 and 3A, living fruit 1000 borne on living tree 104 having inner volume 182 and containing pit 183 is shown having the aroma and rate of emission of the components thereof:

(i) from within the living fruit; and (ii) from the outer surface of the living fruit being analyzed simultaneously with the analysis of the aroma of the inner volume 88 of the living tree 104 and the tree bark surface 10 of the living tree 104 of FIG. 3.

A substantial portion of the outer surface of living fruit 1000 is located at a given distance "$h_F$" (e.g., 0.75") from the central axis and an inner volume 182 surrounds the central axis and is encompassed by the outer surface; and a depth core section 118 is removed from the inner volume 182 along a directional vector "$V_F$" extending substantially radially from the central axis to the outer surface of the living fruit within the inner volume 182. The depth core section 118 has an effective diameter $$2R_{12}$$

(e.g., about ¼") equal to $2\times$(the effective radius $R_{12}$ (about ⅛")) and a core section volume ranging from about $$[\pi R_{12}^2 h_F]$$

down to about $$\left[\frac{\pi R_{12}^2 h_F}{2}\right]$$

thereby forming a core section void within the living fruit. Third analytical apparatus means in FIG. 3 comprises a third trapping tube means (122, 124) which is an outer glass tube 122 and an inner trapping tube 124 inserted through opening 120 into depth core 118. Attached to the trapping tube 124 (which may, for example, contain TENAX ®-GC) is tube 127 connected to third negative pressure pump means 126. Reference numeral 186 represents analytical apparatus capable of providing GC-mass spectra of the trapped substance which may be further taken together with spectral apparatus capable of providing infrared spectra of the trapped substance and spectral apparatus capable of providing NMR spectra of the trapped substance. The apparatus represented by reference numeral 186 is also hereinafter referred to as "third analyzer means".

Fourth analytical apparatus means (for analyzing the aroma emitted from the surface of the living fruit of FIG. 3) comprises fourth trapping tube means 132, 133 inserted into enclosure 134 which enclosure is sealably affixed on surface 138 of the living fruit. The trapping tube means is connected to tube 130 which is connected to negative pressure pump 128 ("fourth negative pressure pump means") associated with analyzer 184 ("fourth analyzer means") (e.g., GC-mass spectral analyzer; nuclear magnetic resonance analyzer; and infrared analyzer). The apparatus is maintained in place in conjunction with the living fruit, e.g., the living fruit shown in FIG. 3 having pit 183 contained therein. The trapping tube 130 is inserted into the enclosure means (e.g., a hemispherically-shaped cup means having an inner cup means void 134 and an outer cup means surface surrounding the void 134 and with the inner volume of said cup means being about:

$$[\tfrac{4}{3}\pi R_{22}{}^3]$$

Thus, when the third negative pressure pump means 126 and the fourth negative pressure pump means 128 are simultaneously engaged, the components of the aroma evolving from the outer surface of the living fruit 1000 are entrapped in the fourth trapping tube means 132 and the third trapping tube means 122 simultaneously, enabling the contents of the third trapping tube means and the fourth trapping tube means to be continuously analyzed using said third and fourth chemical analysis means 186 and 184, respectively. Simultaneously, trapping tube means 24 and 33 enable the analysis by analyzers 86 and 84 to take place of the aroma components of the inner wood section 88 of tree 104 and of the outer bark surface section 38 of tree 104, respectively.

The detailed description of FIGS. 4A and 4B is set forth in the description of Example I, infra.

Referring to FIGS. 5 and 6, there is provided a process for forming scented polymer pellets (wherein the polymer may be a thermoplastic polymer such as low density polyethylene or polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower-most portion of the container is maintained at a slightly lower temperature and the material of the container is taken off at such location for delivery through the conduit. Thus, referring to FIGS. 5 and 6, in particular, the apparatus used in producing such elements comprises a device for forming the polymer containing perfume, e.g., polyethylene or polyethylenepolyvinyl acetate or mixtures of same or polypropylene, or the like, which comprises a vat or container 1212 into which the polymer taken alone or in admixture with other copolymers and a perfuming substance containing at least one of the living tree/fruit fragrances of our invention is placed. The container is closed by means of an air-tight lid 1228 and clamped to the container by bolts 1265. A stirrer 1273 traverses the lid or cover 1228 in an air-tight manner and is rotatable in a suitable manner.

A surrounding cylinder 1212A having heated coils which are supplied with electric current through cable 1214 from a rheostat or control 1216 is operated to maintain the temperature inside the container 1212 such that the polymer in the container will be maintained in the molten or liquid state. It has been found advantageous to employ polymers at such a temperature that the viscosity will be in the range of 9–100 sayboldt seconds.

Heating means (coils 1212A) are operated to maintain the upper portion of the container 1212 within a temperature range of, for example, 250°–260° C. in the case of low density polyethylene. The bottom portion of the container 1212 is also heated by means of heating coils 1212A regulated through the control 1220 connected thereto through a connecting wire 1222 to maintain the lower portion of the container 1212 with a temperature range of 225°–240° C.

Thus, the polymer or mixture of polymers added to the container 1212 is heated from 10–12 hours, whereafter the perfume composition or perfume material containing at least one of the living tree/fruit fragrances of our invention is quickly added to the melt. Generally, about 10–45 percent by weight of the resulting mixture of the perfumery substance is added to the polymer.

After the perfume material containing at least one of the living tree/fruit fragrances of our invention is added to the container 1212, the mixture is stirred for a few minutes, for example, 5–15 minutes and maintained within the temperature ranges indicated previously by the heating coils 1212A. The controls 1216 and 1220 are connected through cables 1224 and 1226 to a suitable supply of electric current for supplying the power for heating purposes Thereafter, the valve "VL" is opened permitting the mass to flow outwardly through conduit 1232 (also indicated by reference numeral 1218 in FIG. 5) having a multiplicity of orifices 1234 adjacent to the lower side thereof The outer end of the conduit 1232 is closed so that the liquid polymer intimately admixed with at least one of the living tree/fruit fragrances of our invention will continuously drop through the orifices 1234 downwardly from the conduit 1232. During this time, the temperature of the polymer intimately admixed with the perfumery substance in the container 1212 is accurately controlled so that a temperature in the range of from about 240°–250° C. (in the case of low density polyethylene) will exist in the conduit 1232. The regulation of the temperature through the controls 1216 and 1220 is essential in order to insure temperature balance to provide for the continuous dropping or dripping of molten polymer intimately admixed with the perfume substance containing at least one of the living tree/fruit fragrances of our invention through the orifices 1234 at a rate which will insure the formation of droplets 1236 which will fall downwardly onto a moving conveyor belt 1238 caused to run between conveyor wheels 1240 and 1242 beneath the conduit 1232. The regulation of the temperature through the controls 1216 and 1220 is essential in order to insure temperature balance to provide for the continuous dropping or dripping of molten polymer intimately admixed with the perfume substance containing at least one of the living tree/fruit fragrances of our invention through the orifices 1234 at a rate which will insure the formation of droplets 1236 which will fall downwardly onto a moving conveyor belt 1238 caused to run between conveyor wheels 1240 and 1242 beneath the conduit 1232.

When the droplets 1236 fall onto the conveyor 1238, they form pellets 1244 which harden almost instantaneously and fall off the end of the conveyor 1238 into a container 1250 which is advantageously filled with water or some other suitable cooling liquid to insure the rapid cooling of each of the pellets 1244. The pellets 1244 are then collected from the container 1250 and utilized for formation of other functional products, e.g., garbage bags and the like.

The following examples are illustrative of processes for carrying out production of flavor and fragrance formulations of our invention and processes for using the living tree/fruit fragrances and flavors of our invention. These examples are illustrative and the invention is to be considered to be restricted thereto only as indicated in the appended claims.

All parts and percentages given herein are by weight unless otherwise specified.

EXAMPLE I

Headspace Sampling and the Analysis of the Interior and Exterior of a Living Tree

Objective

To analyze the headspace of the exterior and interior of a living Douglas Fir tree to determine, through GC/MS analysis, the difference between the interior and exterior volatile headspace constituents.

Procedure

A mature Douglas Fir tree approximately 18 feet tall and 8 inches in diameter at the base was chosen for headspace sampling and is the subject of the instant investigation.

A ¼ inch hole was drilled half way through the base of the tree to a depth of approximately 4 inches. A glass tube 5 inches × ¼ inch outer diameter was then inserted 3.5 inches into the drilled hole of the tree. A ⅛ inch diameter × 4 inch long TENAX ® headspace trap was then placed into the hollow glass tube that was inserted into the tree. An alpha-2 pump (vacuum pump) was then attached to the trap and sampling begun.

Simultaneously, a clear spot was chosen opposite the interior sampling port at the base of the tree. A 25 ml × ½ inch clam shell headspace sampling apparatus was wired to the base of the tree.

Odorless tissue was stuffed around the glass clam shell apparatus where it touched the tree to insure a good seal. A TENAX ® headspace trap was inserted into the glass apparatus and was attached to a second alpha-2 pump. Both pumps were engaged simultaneously causing a flow rate of air through the traps of 40 ml/min. The pumps were operated for a period of seven hours. At the end of the seven hour period, the pumps' operation was terminated and the traps were opened and contents analyzed. The contents of the traps were analyzed by GC-MS analysis using a 50M × 0.32 mm OV-2 fused silica column having conditions: 50°–220° C. at 3° C. per minute.

FIG. 4A is the GC-mass spectrum for the interior (sap wood) section of the Douglas Fir. The peak indicated by reference numeral 200 is the peak for alpha-pinene. The peak indicated by reference numeral 202 is the peak for beta-pinene. The peak indicated by reference numeral 204 is the peak for myrcene. The peak indicated by reference numeral 206 is the peak for limonene. The peak indicated by reference numeral 208 is the peak for thymol methyl ether. The peak indicated by reference numeral 210 is the peak for longifolene.

FIG. 4B is the GC-mass spectrum for the exterior headspace as indicated to be trapped, supra. The peak indicated by reference numeral 220 is the peak for alpha-pinene. The peak indicated by reference numeral 222 is the peak for beta-pinene. The peak indicated by reference numeral 224 is the peak for myrcene. The peak indicated by reference numeral 226 is the peak for limonene. The peak indicated by reference numeral 228 is the peak for thymol methyl ether. The peak indicated by reference numeral 230 is the peak for longifolene.

The peak indicated by reference numeral 232 is the peak for a bisabolene isomer.

The entrapped interior and exterior Douglas Fir tree headspace analysis is set forth in detail as follows:

TABLE I

| Compound Identified | Interior % (AN) | Exterior % (AN) |
|---|---|---|
| Toluene | 0.72 | 0.62 |
| Hexanol, N | 0.10 | — |
| Methyl-2-Methyl Butyrate | — | 0.07 |
| 1,3,5-Heptatriene | — | 0.02 |
| Furfural | Trace | — |
| Aldehyde C-6 | — | 0.03 |
| Ethyl Butyrate | — | 0.04 |
| Tetrachloroethylene | 0.06 | 0.01 |
| Ethyl-2-Methyl Butyrate | Trace | 0.22 |
| Ethyl Isovalerate | Trace | 0.22 |
| Xylene (Isomers) | 0.20 | 0.10 |
| 5-Hexenal, 4-Methylene | Trace | 0.04 |
| Styrene | Trace | 0.01 |
| Nonane, N | Trace | — |
| Benzaldehyde | 0.01 | 0.03 |
| Alpha Pinene | 1.37 | 1.00 |
| Phenol | Trace | 0.01 |
| Beta Phellandrene | 0.05 | 0.02 |
| Beta Pinene | 6.31 | 4.83 |
| Myrcene | 20.61 | 21.18 |
| Alpha Phellandrene | 0.25 | 0.47 |
| Para Cymene | 0.31 | 0.48 |
| Limonene | 65.09 | 63.01 |
| Gamma Terpinene | — | 0.04 |
| Alpha, Para Dimethyl Styrene | 0.22 | 0.40 |
| Terpinolene | 0.02 | 0.47 |
| Para Cresol | 0.02 | 0.01 |
| Homo Ocimene | Trace | 0.01 |
| 4-Isopropyl-2-Cyclohexen-1-One | — | 0.09 |
| Para-Menthe-8-ene-Epoxide | — | 0.16 |
| Cyclohexene, 4-Acetyl-1-Methyl | Trace | — |
| Citronellal | — | 0.02 |
| Ethyl Benzoate | — | Trace |
| Para Methyl Acetophenone | Trace | Trace |
| 4-Isopropyl-2-Cyclohexen-1-One | Trace | 0.25 |
| 8-Cymenol | Trace | 0.10 |
| Myrtenal | Trace | 0.10. |
| Estragole | — | Trace |
| Alpha Terpineol | Trace | 0.05 |
| Neral | Trace | 0.13 |
| Carveol | 0.05 | 0.09 |
| Cuminyl Aldehyde | 0.01 | — |
| Isopropyl Benzaldehyde, Para | 0.10 | 0.10 |
| Thymol Methyl Ether | 0.37 | 0.53 |
| Para Mentha-1,8 Diene-3-One | — | 0.02 |
| Perillaldehyde | 0.01 | 0.02 |
| 1,5-Cyclohexadiene-1-Methanol, 4-(1-Methyl, Ethyl) | — | 0.03 |
| 2-Allyl-3,4(or 5)-Dimethyl-2-Cyclopenten-1-One | — | 0.01 |
| Anethole | — | 0.01 |
| Cuminyl Alcohol | — | 0.01 |
| Carvacrol | 0.01 | — |
| Bornyl Acetate | 0.12 | 0.11 |
| Myrtenal Acetate | 0.02 | 0.01 |
| Citronellyl Acetate | 0.07 | 0.13 |
| Neryl Acetate | Trace | 0.01 |
| Longipinene | 0.11 | 0.32 |
| Geranyl Acetate | 0.05 | 0.12 |
| Alpha Y Angene | 0.02 | 0.10 |
| Longicyclene | 0.01 | 0.06 |
| Sativen | 0.02 | 0.09 |
| Longifolene Isomer | 0.01 | 0.02 |
| Longifolene | 0.39 | 1.31 |
| Bergamotene | Trace | 0.05 |
| Beta Selinene | — | 0.01 |
| Beta Caryophyllene | — | 0.06 |
| Beta Bisabolene | Trace | 0.18 |
| Benzyl Salicylate | — | Trace |
| Hexadecanol | — | Trace |
| | 96.71 | 97.66 |

EXAMPLE II

As a result of the foregoing analysis as set forth in Table I, the following fragrance formulation was prepared using the major components of the "interior" analysis:

| Ingredients | Parts by Weight |
| --- | --- |
| Alpha-Pinene | 1.37 |
| Beta-Pinene | 6.31 |
| Myrcene | 20.61 |
| Limonene | 65.09 |

The resulting fragrance has an intense and substantive natural pine aroma. Accordingly, the fragrance can be described as a "pine fragrance with floral topnotes and undertones".

EXAMPLE III

As a result of the foregoing analysis as set forth in Table I, the following fragrance formulation was prepared using the major components of the "exterior" headspace:

| Ingredients | Parts by Weight |
| --- | --- |
| Alpha-Pinene | 1.00 |
| Beta-Pinene | 4.83 |
| Myrcene | 21.18 |
| Limonene | 63.01 |
| Thymol Methyl Ether | 0.53 |
| Longifolene | 1.31 |

The resulting fragrance has an intense and substantive pine aroma. Accordingly, the fragrance can be described as a "pine fragrance with floral topnotes and undertones".

EXAMPLE IV

As a result of the foregoing analysis as set forth in Example I, in Table I the following fragrance formulation was prepared using the major components of the "exterior" and "interior" headspaces:

| Ingredients | Parts by Weight |
| --- | --- |
| Alpha Pinene | 2.37 |
| Beta Pinene | 11.05 |
| Myrcene | 42.10 |
| Limonene | 128.10 |
| Thymol Methyl Ether | 0.90 |
| Longifolene | 1.71 |

The resulting fragrance has an intense and substantive natural pine aroma. Accordingly, the fragrance can be described as "a pine fragrance with floral topnotes and undertones".

EXAMPLE V

Preparation of a Soap Composition

100 Grams of soap chips are admixed with 1 gram of one of the perfume substances of Table II below until a substantially homogeneous composition is obtained. The perfumed soap manifests an excellent aroma as set forth in Table II below:

TABLE II

| Perfume Ingredients | Aroma |
| --- | --- |
| Perfume composition of Example II. | Pine fragrance with floral topnotes and undertones. |
| Perfume composition of Example III. | Pine fragrance with floral topnotes and undertones. |
| Perfume composition of Example IV. | Pine fragrance with floral topnotes and undertones. |

EXAMPLE VI

Preparation of a Cologne and Handkerchief Perfume

One of the perfume substances as set forth in Table II of Example V is incorporated into a cologne at concentrations of 1.5%, 2.0%, 2.5%, 3.0%, 3.5% and 4.0% in 80%, 85%, 90% and 95% aqueous ethanol and into handkerchief perfumes at concentrations of 15%, 20%, 25% and 30% (in 85%, 90% and 95% aqueous ethanol). Distinct and definite fragrances as set forth in Table II of Example V are imparted to the cologne and to the handkerchief perfume at each of the levels indicated.

EXAMPLE VII

Preparation of a Cosmetic Powder Composition

A cosmetic powder is prepared by mixing in a ball mill, 100 grams of talcum powder with 0.15 grams of one of the substances of Table II of Example V. The resulting powders have excellent aromas as set forth in Table II of Example V.

EXAMPLE VIII

Utilizing the procedure of Example I of Column 15 U.S. Pat. No. 3,632,396 the specification for which is incorporated by reference herein, a non-woven cloth substrate useful as a drier-added fabric-softening article of manufacture is prepared wherein the substrate, the substrate coating and the outer coating and the perfuming material are as follows:

1. a water "dissolvable" paper ("Dissolvo paper");
2. Adogen 448 (m.p. about 140° F.) as the substrate coating; and
3. an outer coating having the following formulation (m.p. about 1.50° F.):
   57 percent—C20-22HAPS
   27 percent—isopropyl alcohol
   20 percent—antistatic agent
   1 percent—of one of the perfume substances of Table II of Example V.

Fabric-softening compositions prepared as set forth above having an aroma characteristic as set forth in Table II of Example V essentially consists of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substrate. Aromas are imparted as set forth in Table II of Example V in a pleasant manner to the headspace in the dryer on operation thereof using the said dryer added fabric softening non-woven fabric.

EXAMPLE IX

Preparation of a Soap Composition

100 Grams of soap chips are prepared according to Example V of U.S. Pat. No. 4,058,490 issued on Nov.

15, 1977 the specification for which is incorporated herein by reference, as follows:

"The sodium salt of an equal mixture of $C_{10}$-$C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water 0.2 lb. titanium hydroxide."

The resulting blend is then mixed with one of the perfume substances of Table II of Example V until a substantially homogeneous composition is obtained. The perfumed soap composition manifests an aroma as set for in Table II of Example V.

EXAMPLE X

Granular Detergent Composition

A granular detergent composition is prepared according to United Kingdom Patent No. 1,501,498 the specification for which is incorporated by reference herein having the following formula. It is prepared by spray-drying the following mixture:

| Ingredient | Parts by Weight |
| --- | --- |
| Sodium salt of ethoxylated fatty alcohol sulfate having an average of about 2.25 moles of ethylene oxide per mole of fatty alcohol | 14.1 |
| Sodium tallow alkyl sulfate | 2.4 |
| Sodium silicate solids ratio $SiO_2/Na_2O = 2.0$ | 6.0 |
| Sodium tripolyphosphate | 24.0 |
| $Na_{12}(AlO_2SiO_2)27H_2O$ | 18.0 |
| Moisture | 10.0 |
| Sodium sulfate | 25.0 |
| Perfume substance of Table II of Example V. | 4.0 |

Laundry solutions containing the above detergent compositions are used to launder fabrics. Each of the laundry compositions both prior to and on laundering give rise to a pleasant aroma as set forth in Table II of Example V.

EXAMPLE XI

Perfumed Liquid Detergent

Concentrated liquid detergents are prepared with aromas as set forth in Table II of Example V containing 0.10%, 0.15% and 0.20% of each of the substances of Table II of Example V in the liquid detergent. The liquid detergent is a builder free liquid detergent consisting of (a) 50% of a nonionic surfactant having a HBL of 8.0 and a critical micelle concentration of 0.007 weight percent at 25° C.; (b) an anionic surfactant which is a triethanolamine prepared according to United Kingdom Patent No. 1,491,603 the specification for which is incorporated by reference herein.

The detergents all possess aromas as set forth in Table II of Example V, supra.

EXAMPLE XIIV

Preparation of a Detergent Composition

A total of 100 grams of detergent powder (a low phosphate content detergent composition which contains 12% by weight phosphate builder, 8 percent hardness mineral ion insensitive detergent, 0.9 percent by weight maleic anhydride-vinyl compound co-polymer and 2 percent alkylene oxide condensation product prepared according to Example IV at column IX, U.S. Pat. No. 4,000,080 issued on Dec. 28, 1976, the specification for which is incorporated by reference herein) is intimately admixed with 0.15 grams of one of the perfume materials of Table II of Example V, supra, until a substantially homogeneous composition is obtained. The composition has an aroma as set forth in Table II of Example V, supra.

EXAMPLE XIII

Each of the fragranced material of Table II of Example V, supra, are added to a 50:50 weight:weight mixture of low density polyethylene:polyepsilon caprolactone PCL-700 forming pellets with scents as set forth in Table II of Example V, supra.

75 Pounds of a mixture of PCL-700 polyepsilon caprolactone (manufactured by the Union Carbide Corporation of New York, N.Y having a melting point of about 180°-190° F.): low density polyethylene are heated to about 250° C., in a container of the kind illustrated in FIGS. 5 and 6. 25 Pounds of each of the fragrance materials as set forth in Table II of Example V is then quickly added to the liquified polymer mixture, the lid 228 is put in place and the agitating means 273 are actuated. The temperature is then raised to about 260° F. and the mixing is continued for 5-15 minutes. The valve "VL" is then opened to allow flow of the molten polymer enriched with perfume ingredient to exit through the orifices 234. The liquid falling through the orifices 234 solidified almost instantaneously upon impact with the moving cooled conveyor 238. Polymer beads or pellets 244 having pronounced scents as described in Table II of Example V, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example V, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table II of Example V, supra.

EXAMPLE XIV

Each of the LIVING TREE/FRUIT ™ perfume compositions of Table II of Example V are individually admixed with CLARYCET ™ (trademark of International Flavors & Fragrances Inc. for the ester having the structure:

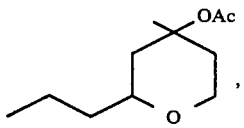

in the ratio of 10 parts by weight of ester to one part by weight of LIVING TREE/FRUIT ™ perfume composition. At the rates of:
- 100 ppm;
- 150 ppm; and
- 200 ppm.

The resulting composition is added to EXXON ® middle distillate fuel heating oil in accordance with the procedure of European Published Application 532556 published on Mar. 24, 1990 (corresponding to PCT Application 91/18961-A).

On use, in each case, the unpleasant "burnt fuel oil" nuances are completed masked and "faint pleasant aromas" described in Table II of Example V are imparted to the environments surrounding the burning heating oil.

EXAMPLE XV

Raspberry Flavor Formulation

The following basic raspberry flavor formulation is produced:

| Ingredients | Parts by Weight |
| --- | --- |
| Vanillin | 2.0 |
| Maltol | 5.0 |
| Parahydroxybenzylacetone | 5.0 |
| Alpha-ionone (10% in propylene glycol) | 2.0 |
| Ethyl Butyrate | 6.0 |
| Ethyl Acetate | 16.0 |
| Dimethyl Sulfide | 1.0 |
| Isobutyl Acetate | 13.0 |
| Acetic Acid | 10.0 |
| Acetaldehyde | 10.0 |
| Propylene Glycol | 930.0 |

The living tree (exterior) composition produced according to Example II is added to half of the above formulation at the rate of 0.2%. The second half does not contain the living tree (interior) composition. The formulation with the living tree composition produced according to Example II is compared with the formulation without the living tree composition produced according to Example II at the rate of 0.01% (100 ppm) in water and evaluated by a bench panel.

The flavor containing the living tree composition produced according to Example II is found to have a substantially more pleasant and better raspberry aroma. It is the unanimous opinion of the bench panel that the living tree composition produced according to Example II, rounds the flavor out and contributes to a very natural fresh aroma and taste as found in full ripe raspberries. Accordingly, the flavor with the addition of the living tree composition produced according to Example II is considered as substantially better than the flavor without the living tree composition produced according to Example II.

EXAMPLE XVI

The following formulations are produced:
Formulation A
1.9 gm Natural black currant juice, concentrate
0.1 gm Natural black currant esters
10.0 ml Sugar Syrup 32° Be
g.s. 100 ml Spring water
Formulation B
1.9 gm Natural black currant juice, concentrate
0.1 gm Buchu leaf oil 0.1% (ethanol 95%)
10.0 ml Sugar Syrup 32° Be
e.s. 100 ml Spring water
Formulation C
1.9 gm Natural black currant juice, concentrate
0.1 gm Niribine* 10% (ethanol 95%)
10.0 ml Sugar Syrup 32Be
g.s. 100 ml Spring water

*Niribine is produced by distilling an alcoholic macerate of black currant buds.

Formulation D
1.9 gm Natural black currant juice, concentrate
0.1 gm Living tree composition of Example III
10.0 ml Sugar Syrup 32Be
g.s. 100 ml Spring water
Formulation E
1.9 gm Natural black currant juice, concentrate
10.0 ml Sugar Syrup 32Be
g.s. 100 ml Spring water Each of the above-mentioned formulations is compared with one another by a panel composed of 10 tasters. Formulation E is generally considered by the panel to be flat and not very characteristic for fresh black currant. Formulations B, C and D are considered as having substantially fresh and more pleasant notes than formulation E. In summary, formulation D is preferred as the best black currant flavor, the living tree composition of Example III can be used at rates of one-tenth of that of Buchu leaf oil in black currant juice.

It is further to be concluded that living tree composition of Example III can successfully replace Buchu leaf oil, Niribine and/or natural black currant esters wherever the ingredient is used in reinforced black currant juices, substitued black currant juices and imitation black currant flavors.

EXAMPLE XVII

Basic Black Currant Formulation

The living tree composition of Example IV has been added to a basic black currant flavor formulation at the rate of 1.5%. Both flavors have been compared in water at the rate of 200 ppm and evaluated by a bench panel.

The flavor containing the living tree composition of Example IV has had the characteristic aroma and taste of ripe black currants or fresh black currant juice. The typical note was not present in the basic black currant formulation. Therefore all members of the panels preferred the flavor containing the living tree composition of Example IV. Detailed below is a basic black currant formulation to which is added the living tree composition of Example IV at the rate of 1.5%:

| Ingredients | Parts by Weight |
| --- | --- |
| Cis-3-hexen-1-ol | 5.0 |
| Alpha-phellandrene | 1.5 |
| Tepineol-4 10% (in ethyl alochol) | 3.0 |
| Para-hydroxy benzyl acetone | 5.0 |
| Vanillin | 2.0 |
| Ethyl maltol | 6.0 |
| Methyl benzoate | 2.0 |
| Benzaldehyde | 2.0 |
| Benzylpropinoate | 4.0 |
| Isobutylacetate | 5.0 |
| Coriander oil | 0.5 |

-continued

| Ingredients | Parts by Weight |
|---|---|
| Ethylbutyrate | 8.0 |
| Dimethylsulfide | 3.0 |
| Fusel oil | 8.0 |
| Acetic acid | 10.0 |
| Alpha-ionone 10% (in ethyl alcohol) | 0.5 |
| Ethyl heptanoate | 0.5 |
| Propylene glycol | 934.0 |
| | 1000.0 |

EXAMPLE VIII

Grapefruit Flavor

The following formulation is prepared:

| Ingredients | Parts by Weight |
|---|---|
| Grapefruit oil | 92 |
| Bergamot oil | 2 |
| Citral | 3 |
| Amyl alcohol | 1 |
| Ethyl acetate | 1 |
| Living tree composition of Example III | 1 |

When the above grapefruit formulation is added to water at the rate of 1%, an excellent grapefruit drink is prepared. The living tree composition of Example III gives a fruitier peeliness to the instant formulation thereby rendering it more desirable. The living tree composition of Example III can also be rendered by using 0.5 parts of the living tree composition of Example II.

EXAMPLE XIX (A) 120 Grams of the flavor composition of Example XVII is emulsified in a solution containing 300 gm gum acacia and 700 gm water. The emulsion is spray-dried with a Bowen Lab Model Drier utilizing 250 c.f.m. of air with an inlet temperature of 500° F., an outlet temperature of 200° F., and a wheel speed of 50,000 r.p.m..

(B) The following mixture is prepared:

| Ingredients | Parts by Weight |
|---|---|
| Liquid flavor composition of Example XVII | 25 |
| Propylene glycol | 1 |
| Cab-O-Sil M-5 (Brand of Silica produced by the Cabot Corporation of 125 High Street, Boston, Massachusetts 02110 Physical properties: Surface area: 200 m/gm Nominal Particle size: 0.012 microns Density: 2.3 lbs/cu. ft.) | 3 |
| Ethyl cellulose | 8 |

The Cab-O-Sil and ethyl cellulose is dispersed in the liquid flavor composition of Example XVII with vigorous stirring, thereby resulting in a viscous liquid. 65 Parts by weight of the powder flavor composition of Part A is then blended into said viscous liquid, with stirring, at 25° C. for a period of 30 minutes resulting in a dry, free flowing, sustained release flavor powder.

EXAMPLE XX

Chewing Gum

100 Parts by weight of chicle are mixed with 4 parts by weight of the flavor prepared in accordance with Example XIX. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting black currant flavor.

EXAMPLE XXI

Chewable Vitamin Tablets

The flavor material produced according to Example XIX is added to a Chewable Vitamin Tablet Formulation at a rate of 5 gm/Kg which Chewable Vitamin Tablet Formulation is prepared as follows:

In a Hobert Mixer, the following materials are blended to homogeneity:

| | Gms/1000 Tablets |
|---|---|
| Vitamin C (ascorbic acid) as ascorbic acid sodium ascorbate mixture 1:1 | 70.0 |
| Vitamin $B_1$ (thiamine mononitrate) as Rocoat thiamine mononitrate 33⅓% (Hoffman La Roche) | 4.0 |
| Vitamin $B_2$ (riboflavin) as Rocoat riboflavin 33⅓% | 5.0 |
| Vitamin $B_2$ (pyridoxine hydrochloride) as Rocoat pyridoxine hydrochloride 33⅓% | 4.0 |
| Niacinamide as Rocoat niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example XIX | 2.5 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g Dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong black currant flavor for a period of 12 minutes.

What is claimed is:

1. A process for the preparation of a flavor or fragrance composition by means of first quantitatively and qualitatively substantially continuously analyzing the aroma emitted and rate of emission of the components thereof:

(i) from within the inner wood section and/or pith section; and (ii) from the outer tree bark surface of a living tree simultaneously and then providing at least the major aroma components found in at least one of said analyses and admixing the resulting components, consisting essentially of the steps of:

(a) providing at least one living tree having a trunk or tree limb located on a given central axis, said trunk or tree limb having an outer surface, a substantial portion of which is located at a given distance, "h" from said central axis and an inner volume surrounding said central axis and encompassed by said outer tree bark surface;

(b) removing at least one depth core section from said inner volume running from said outer surface to a depth of from about "$\frac{1}{2}$h" up to "h" into said inner volume along a directional vector "V" extending substantially radially from said central axis to said outer tree bark surface within said inner volume, said depth core section having an effective diameter $D_1$ equal to $2 \times$ (effective radius, $R_1$) and a core section volume ranging from about $[\pi R_1^2 h]$;

down to about $$\left[\frac{\pi R_1^2 h}{2}\right]$$

thereby forming at least one core section void within said living tree trunk or tree limb; then
(c)-1: providing first analytical apparatus means comprising first trapping tube means attached to first negative pressure pump means associated with first chemical analysis means;
(c)-2: providing second analytical apparatus means comprising a second trapping tube means attached to second negative pressure pump means associated with second chemical analysis means;
(d) providing a hollow flexible enclosure means having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer tree bark surface of said living tree at said enclosure rim means;
(e) causing said enclosure means to sealably grip said portion of said outer tree bark surface of said living tree at said enclosure rim means;
(f) inserting said first trapping tube means into said core section void along said directional vector "V";
(g) inserting said second trapping tube means through said insertion orifice, causing it to be extended into said enclosure means void;
(h) simultaneously engaging said first negative pressure pump means and said second negative pressure pump means whereby components of the aroma evolving from said outer tree bark surface of said living tree are entrapped in said second trapping tube means and components of the aroma evolving from within said living tree are entrapped in said first trapping tube means, simultaneously;
(j) analyzing the contents of said first trapping tube means using said first chemical analysis means and said second trapping tube means using said second chemical analysis means substantially continuously and substantially simultaneously; and
(k) providing from at least one independent source at least the major aroma components found in at least one of the two analyses of step (j); and
(l) admixing the resulting components to form a perfume composition and/or a flavor composition.

2. The process of claim 1 wherein the living tree is a living Douglas Fir.

3. The process of claim 1 wherein:
(a) the living tree is bearing living fruit; and
(b) the outer surface and the inner volume of the living fruit are analyzed simultaneously with the analysis of the outer tree bark surface and inner wood section and/or pith section of the living tree.

* * * * *